US009894895B2

(12) United States Patent
Santra et al.

(10) Patent No.: US 9,894,895 B2
(45) Date of Patent: Feb. 20, 2018

(54) NON-PHYTOTOXIC COMPOSITE POLYMER FILM BARRIER AS A REPELLENT FOR CONTROLLING INFECTION

(71) Applicant: University of Central Florida Research Foundation, Inc., Orlando, FL (US)

(72) Inventors: Swadeshmukul Santra, Orlando, FL (US); Mikaeel Young, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 14/713,027

(22) Filed: May 15, 2015

(65) Prior Publication Data

US 2015/0342194 A1    Dec. 3, 2015

Related U.S. Application Data

(60) Provisional application No. 61/993,347, filed on May 15, 2014.

(51) Int. Cl.
    *A01N 25/00*      (2006.01)

(52) U.S. Cl.
    CPC ................... *A01N 25/00* (2013.01)

(58) Field of Classification Search
None
See application file for complete search history.

(56) References Cited

U.S. PATENT DOCUMENTS

| 9,247,734 | B2 | 2/2016 | Sabin | |
|---|---|---|---|---|
| 9,717,251 | B2 | 8/2017 | Sabin | |
| 9,718,739 | B2 | 8/2017 | Sabin | |
| 2003/0022574 | A1* | 1/2003 | Pesce | ...................... A61L 15/28 442/96 |
| 2009/0233077 | A1* | 9/2009 | Advincula | ............. C09D 5/006 428/304.4 |

FOREIGN PATENT DOCUMENTS

JP      04146942 A   *   5/1992

OTHER PUBLICATIONS

Translation of JP 04146942 A, May 1992.*

* cited by examiner

*Primary Examiner* — Carlos Azpuru
*Assistant Examiner* — Casey Hagopian
(74) *Attorney, Agent, or Firm* — Bond, Schoeneck & King, PLLC; William Greener; Alek Szecsy

(57) ABSTRACT

Embodiments of the present disclosure relate to organo-silica based composite materials, methods of making the organo-silica based composite material, methods of using the organo-silica based composite material, and the like.

38 Claims, 6 Drawing Sheets

(OSCF nanogel)

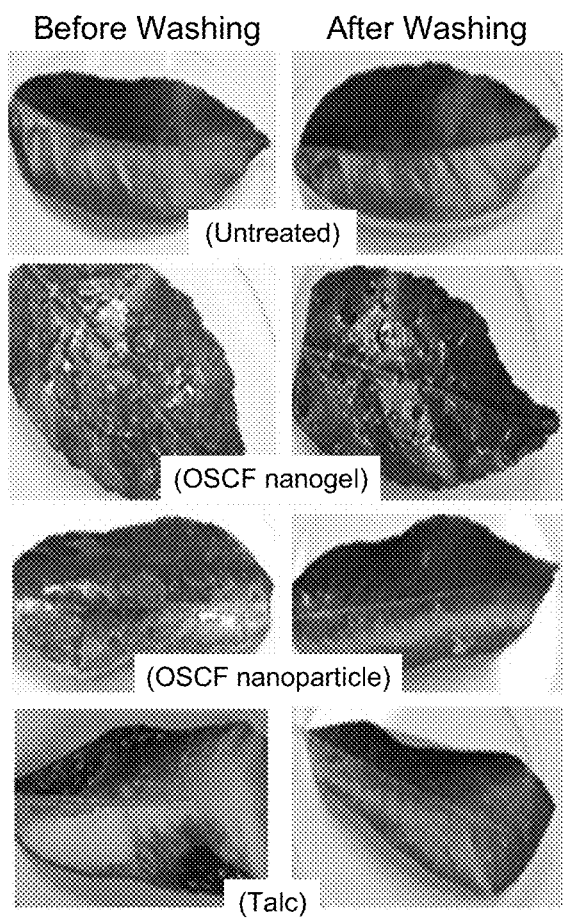
Before Washing  After Washing
FIG. 1A (Untreated)
FIG. 1B (OSCF nanogel)
FIG. 1C (OSCF nanoparticle)
FIG. 1D (Talc)
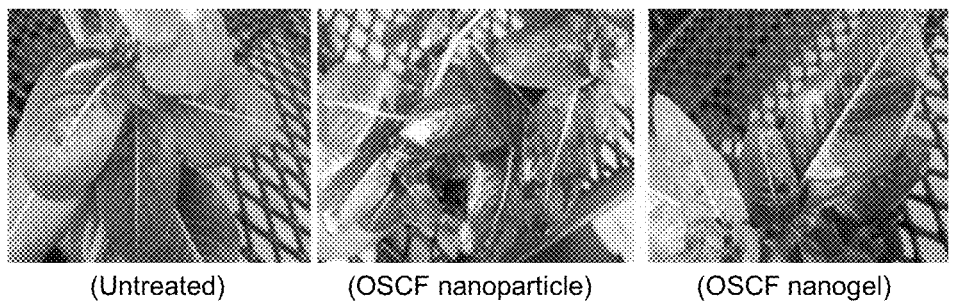
(Untreated)      (OSCF nanoparticle)   (OSCF nanogel)
FIG. 2A          FIG. 2B               FIG. 2C

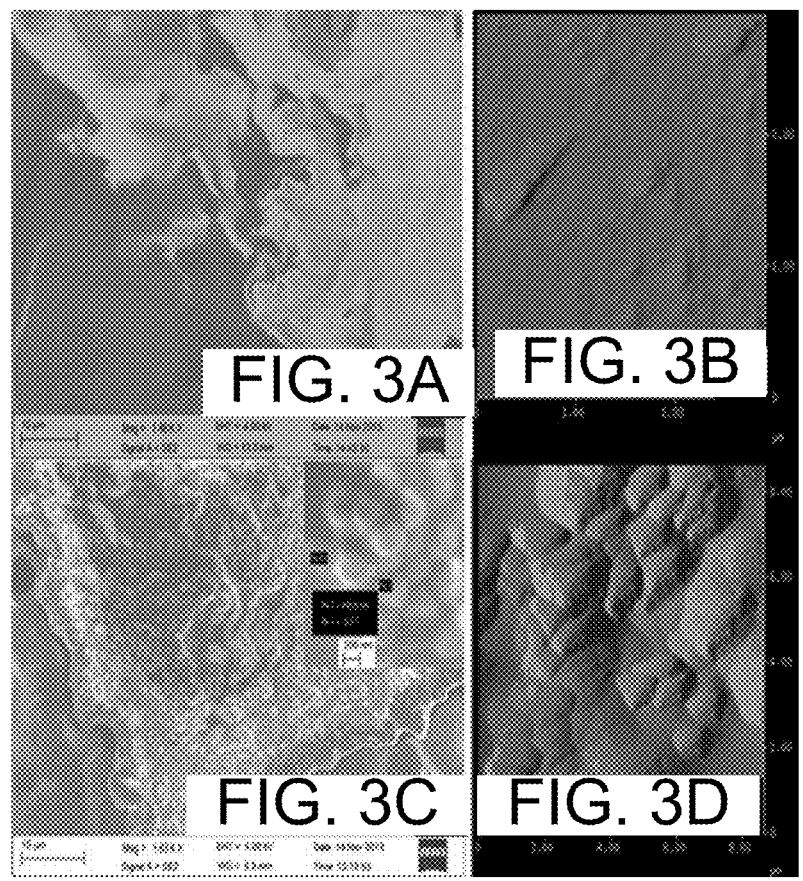

NON-PHYTOTOXIC COMPOSITE POLYMER FILM BARRIER AS A REPELLENT FOR CONTROLLING INFECTION

CLAIM OF PRIORITY TO RELATED APPLICATION

This application claims priority to U.S. provisional application entitled "NON-PHYTOTOXIC COMPOSITE POLYMER FILM BARRIER AS ACP REPELLENT FOR CONTROLLING HLB INFECTION" having Ser. No. 61/993,347, filed on May 15, 2014, which is entirely incorporated herein by reference.

BACKGROUND

The globalization of business, travel and communication brings increased attention to worldwide exchanges between communities and countries, including the potential globalization of the bacterial and pathogenic ecosystem. Bactericides and fungicides have been developed to control diseases in man, animal and plants, and must evolve to remain effective as more and more antibiotic, pesticide and insecticide resistant bacteria and fungi appear around the globe.

Bacterial resistance to antimicrobial agents has also emerged, throughout the world, as one of the major threats to both man and the agrarian lifestyle. Resistance to antibacterial and antifungal agents has emerged as an agricultural issue that requires attention and 20 improvements in the treatment materials in use today.

For example, focusing on plants, there are over 300,000 diseases that afflict plants worldwide, resulting in billions of dollars of annual crop losses. The antibacterial/antifungal formulations in existence today could be improved and made more effective.

SUMMARY

Embodiments of the present disclosure relate to organo-silica based composite materials (also referred to as a "composite material"), methods of making the organo-silica based composite material, methods of using the organo-silica based composite material (e.g., treating or preventing disease or disease transmission in plants), and the like.

An embodiment of the present disclosure includes a composite material, among others, that includes: a silicon based material and a polymer, wherein the polymer is selected from the group consisting of: polyvinylpyrrolidone, polyacrylamide, polylactic acid, polyglycolic acid, chitosan, dextran, polyethyleneglycol, polyvinylalcohol, and a combination thereof.

An embodiment of the present disclosure includes a method, among others, that includes: disposing a composite material on a surface, wherein the composite material includes: a silicon based material and a polymer, wherein the polymer is selected from the group consisting of: polyvinylpyrrolidone, polyacrylamide, polylactic acid, polyglycolic acid, chitosan, dextran, polyethyleneglycol, polyvinylalcohol, and a combination thereof; and inhibiting or substantially inhibiting the transmission of a plant disease. In an embodiment, the disease can be HLB or Pierce's disease.

An embodiment of the present disclosure includes a method, among others, that includes: disposing a composite material on a surface to form a film on the surface in situ, wherein the composite material includes: a silicon based material and a polymer, wherein the polymer is selected from the group consisting of: polyvinylpyrrolidone, polyacrylamide, polylactic acid, polyglycolic acid, chitosan, dextran, polyethyleneglycol, polyvinylalcohol, and a combination thereof; and preventing or substantially preventing ACPs from transmitting HLB or Sharpshooter from transmitting Pierce's disease.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure.

FIGS. 1A-to 1D illustrate a rainfastness study of OSCF materials. FIG. 1A illustrated untreated, FIG. 1B illustrates OSCF nanogel, and FIG. 1C illustrates OSCF nanoparticle film materials, each sprayed on citrus variety, Lime. Under green-house conditions, approximately 5 mL of as synthesized formula was sprayed on plants. Left panel and right panel show digital photograph of leaf surface before and after rainfall simulation (above six inches rain fall). OSCF nanogel exhibited outstanding rainfastness in comparison to OSCF nanoparticle. Other controls such as SiNP-PAM, SiNG-PAM, SiNG, SiNP (data not shown) did show moderate rainfastness. Talc (FIG. 1D) and PAM completely washed off from the leaf surface.

FIGS. 2A to 2C illustrate phytotoxicity (plant tissue injury) results. FIG. 2A illustrates untreated, FIG. 2B illustrates OSCF nanoparticle, and FIG. 2C illustrates OSCF nanogel film materials, sprayed on Vinca. sp. Under green-house conditions, approximately 5 mL of synthesized formula was sprayed on plants at 7:30 AM on the test day. After 72 hrs, all treatments were non-phytotoxic (−) to plants.

FIGS. 3A to 3D illustrate FE-SEM (left panel) and AFM (right panel) images of SiNG-PAM (A, B) and SiNP-PAM (C, D) composite film materials. SiNG clusters embedded in PAM film are clearly seen in the AFM image (B). SiNPs are in the submicron size range (300-400 nm) as seen in both FE-SEM (C) and AFM (D) images. The inset of FE-SEM image (C) showing SiNP clusters embedded in the PAM polymer matrix.

DETAILED DESCRIPTION

Figure 4:
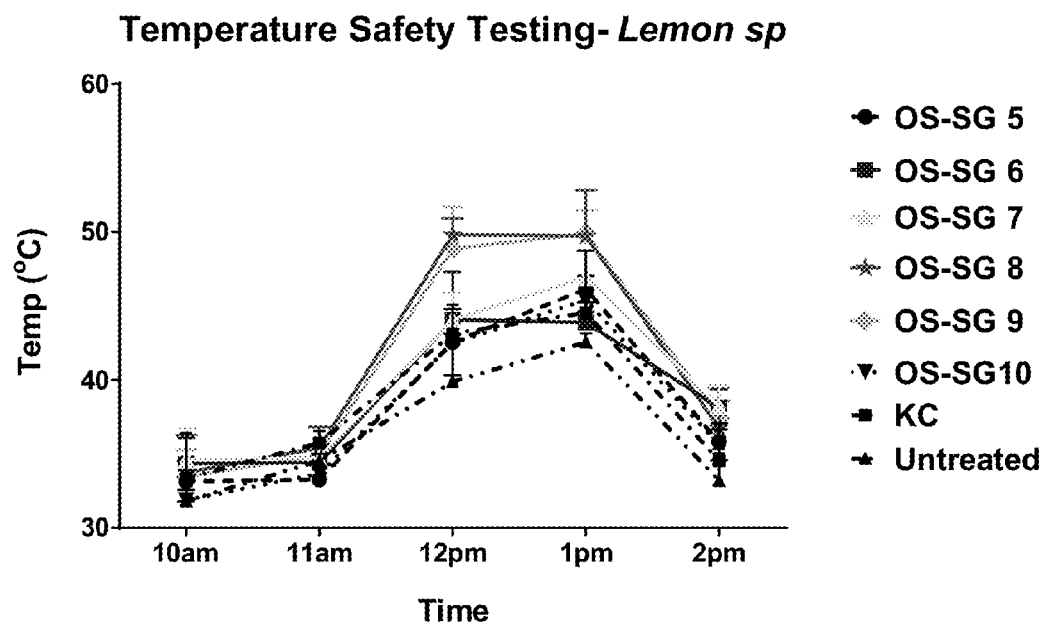
FIG. 4 is a graph illustrating the temperature safety testing for OSCF materials. All OSCF tested except OS-SG 8 and 9 do not exhibit significant temperature variance in comparison to kaolin clay control.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features that may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, polymer chemistry, biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmospheres. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

"Uniform plant surface coverage" refers to a uniform and complete (e.g., about 100%) wet surface due to spray application of embodiments of the present disclosure. In other words, spray application causes embodiments of the present disclosure to spread throughout the plant surface.

"Substantial uniform plant surface coverage" refers to about 70%, about 80%, about 90%, or more uniform plant surface coverage.

"Substantially covering" refers to covering about 70%, about 80%, about 90%, or more, of the leaves and branches of a plant.

"Plant" refers to trees, plants, shrubs, flowers, and the like as well as portions of the plant such as twigs, leaves, stems, branches, fruit, flowers, and the like. In a particular embodiment, the term plant includes a fruit tree such as a citrus tree (e.g., orange tree, lemon tree, lime tree, and the like).

As used herein, "treat", "treatment", "treating", and the like refer to preventing or preventing the spread of a disease (e.g., citrus greening) with a composition of the present disclosure. In addition, "treatment" includes completely or partially preventing (e.g., about 70% or more, about 80% or more, about 90% or more, about 95% or more, or about 99% or more) the transmission of a disease. "Prevent" or "preventing" as used herein, covers one or more treatments of a disease in a plant, and includes: reducing the risk of occurrence of or transmission of the disease in a plant predisposed to the disease but not yet diagnosed as infected with the disease, and the like.

The term "substituted" refers to any one or more hydrogens on the designated atom that can be replaced with a selection from the indicated group, provided that the designated atom's normal valence is not exceeded, and that the substitution results in a stable compound. In an embodiment, the indicated group can include in or more halogens, aliphatic groups, and the like.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon chain and a substituted saturated aliphatic hydrocarbon chain which may be straight, branched, or cyclic, having 1 to 20 carbon atoms, where the stated range of carbon atoms includes each intervening integer individually, as well as sub-ranges. Examples of alkyl groups include, but are not limited to, methyl, ethyl, i-propyl, n-propyl, n-butyl, t-butyl, pentyl, hexyl, heptyl, octyl, nonyl, decyl, and the like. The substitution can be with a halogen, for example.

As used herein, "alkenyl" or "alkenyl group" refers to an aliphatic hydrocarbon which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, hexenyl, heptenyl, octenyl, decenyl, and the like.

The term "alkynyl" refers to straight or branched chain hydrocarbon groups, containing at least one triple carbon to carbon bond having 2 to 20 carbon atoms, wherein the stated range of carbon atoms includes each intervening integer individually, as well as sub-ranges. An alkynyl group can be optionally substituted, unless stated otherwise, with one or more groups.

The term "aryl" refer to aromatic homocyclic (i.e., hydrocarbon) mono-, bi- or tricyclic ring-containing groups preferably having 6 to 12 members such as phenyl, naphthyl and biphenyl. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, etc., where optionally one or more pair of substituents together with the atoms to which they are bonded form a 3 to 7 member ring.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

DISCUSSION

In accordance with the purpose(s) of the present disclosure, as embodied and broadly described herein, embodiments of the present disclosure, in one aspect, relate to environment-friendly non-phytotoxic organo-silica based composite material, methods of making the organo-silica based composite material, methods of using the organo-silica based composite material, and the like.

In an embodiment, the organo-silica based composite material (e.g., also referred to as "composite material") can be used to form a film that can achieve uniform plant or plant part surface coverage, substantial uniform plant or plant part surface coverage, substantially covering the surface of a plant or plant part, substantial uniform plant or plant part surface coverage, or substantially covering a plant or part of a plant. Embodiments of the present disclosure are effective as a barrier for preventing or substantially preventing the transmission a disease affecting plants such as citrus plants and trees.

In an embodiment, the plant disease can include citrus greening (also called Huanglongbing, (HLB)), Pierce's disease and other vector transmitted diseases. In an embodiment, the organo-silica based composite material can be used to prevent or substantially prevent the transmission of HLB, forming a barrier on the surface (e.g., of a plant or plant part), and/or prevent or substantially prevent Asian Citrus Psyllid (ACPs) from transmitting HLB. In another embodiment, the organo-silica based composite material can be used to prevent or substantially prevent the transmission of Pierce's disease, forming a barrier on the surface (e.g., of a plant or plant part), and/or prevent or substantially prevent Sharpshooter (SP) from transmitting Pierce's disease.

In an embodiment, the composite material can be disposed on a surface of a structure. In an embodiment, the structure can include plants such as trees, shrubs, grass, agricultural crops, and the like, includes leaves and fruit. In an embodiment, the composite material provides uniform plant surface coverage, substantial uniform plant surface coverage, or substantially covers the plant or portion (e.g., leaves, flowers, etc.) of the plant.

In an embodiment, the composite material can also be disposed on structures such as, without limitation, fabrics, cooking counters, food processing facilities, kitchen utensils, food packaging, swimming pools, metals, drug vials, medical instruments, medical implants, yarns, fibers, gloves, furniture, plastic devices, toys, diapers, leather, tiles, and flooring materials. In an embodiment, the structure can include textile articles, fibers, filters or filtration units (e.g., HEPA for air and water), packaging materials (e.g., food, meat, poultry, and the like food packaging materials), plastic structures (e.g., made of a polymer or a polymer blend), glass or glass like structures on the surface of the structure, metals, metal alloys, or metal oxides structure, a structure (e.g., tile, stone, ceramic, marble, granite, or the like), and a combination thereof.

An embodiment of the present disclosure includes a composite material made of a silicon based material and a polymer. In an embodiment, the silicon based material can include a silica nanogel, a silica nanoparticle, or combinations thereof. In an embodiment, the silica based material and the polymer can crosslink with one another to form the composite material. When disposed on a surface (e.g., a leaf), the composite material can form a film on the surface. In an embodiment, the polymer can be about 40 to 60 weight % of the dry composite material (e.g., "dry" indicates that the water content is not included in the weight % determination). In an embodiment, the silicon based material can be about 40 to 60 weight % of the dry composite.

In an embodiment, the silica nanogel is prepared using silica precursor materials (e.g., sodium silicate, tetraethyl orthosilicate, tetramethyl orthosilicate, and combinations thereof), where acid catalyzed hydrolysis of the silica precursors produces sol particles which condenses to form the silica nanogel. In an embodiment, the silica nanogel can be represented as a crosslinked system of silica compounds (e.g., RO—Si(OH)$_2$(O$^+$H$_2$, RO—Si(OH)$_2$—O—Si(OH)$_2$ OR, where R can be linear, branched, cyclic, saturated or unsaturated, substituted or unsubstituted, aromatic or aliphatic group). In an embodiment, the silica nanogel can include silica nanoparticles that are interconnected with each other and silica compounds forming a crosslinked system of silica nanoparticles and silica compounds.

In an embodiment, the silica nanoparticles are formed by the base catalyzed hydrolysis of the silica precursor materials, where silica nanoparticles for the sol gel nuclei grow into silica nanoparticles. In an embodiment, the silica nanoparticles can have a diameter of about 5 to 100 nm.

In an embodiment, the polymer can include: polyvinylpyrrolidone, polyacrylamide, polylactic acid, polyglycolic acid, chitosan, dextran, polyethyleneglycol, polyvinylalcohol, and a combination (including copolymers) thereof. In an embodiment, the polymer can be polyacrylamide.

In general, a composite material including the silicon based material and the polymer can be synthesized at room temperature using a sol-gel method as the silica precursor. Hydrolysis and condensation reaction of the silica precursor can be conducted in the presence of the polymer. Additional details regarding methods of synthesis are provided in Example 1.

In an embodiment, the composite material can be a silica nanogel-polymer composite material. In an embodiment, the composite material can be a silica nanoparticle-polymer composite material.

In an embodiment, the composite material can also include a crosslinker, which can increase the crosslinking of the polymer and the silicon based material. In an embodiment, the crosslinker can be a metal ion such as Ca$^{2+}$, Mg$^{2+}$, Zn$^{2+}$, Al$^{3+}$, Cu$^{2+}$, and a combination thereof. The crosslinker can bind to the polymer and silica via a metal-ligand complex. In an embodiment, the metal ion can bind to an amide group of polyacrylamide and the OH group of silica via a metal-ligand complex. In another embodiment, the metal ion can bind to the keto group of the polyvinylpyrrolidone and the OH group of silica via a metal-ligand complex.

In an embodiment, the crosslinker can be about 10 to 20 weight % of the dry composite. In an embodiment, the crosslinker can be about 10 to 20 weight % of the dry composite, the polymer is about 30 to 40 weight % of the dry composite, and the silicon based material is about 30 to 40 weight % of the dry composite.

In an embodiment, the composite material can be a silica nanogel-crosslinker-polymer composite material. In an embodiment, the composite material can be a silica nanoparticle-crosslinker-polymer composite material.

In general, a composite material including the silicon based material, crosslinker, and the polymer can be synthesized at room temperature using a sol-gel method as the silica precursor. Hydrolysis and condensation reaction of the silica precursor can be conducted in the presence of the polymer and the crosslinker. Additional details regarding methods of synthesis are provided in Example 1.

In an embodiment, the composite material can include a material such as kaolin, ZnO, or a combination thereof. In an embodiment, the polymer, silicon based material and the material can crosslink with one another via intermolecular forces (van der Waal's interaction) such as hydrogen bonding, dipole-dipole interaction, dipole-induced dipole interaction and induced dipole-induced dipole interaction (London dispersion force) or a combination thereof, to form the composite material. In an embodiment, the material can be about 10 to 40 weight % of the dry composite. In an embodiment, the material can be about 10 to 40 weight % of the dry composite, the polymer can be about 20 to 50 weight % of the dry composite, and the silicon based material can be about 20 to 40 weight % of the dry composite.

In an embodiment, the composite material can be a kaolin-silica nanogel-polymer composite material. In an embodiment, the composite material can be a ZnO-silica nanogel-polymer composite material.

In general, a composite material including the silicon based material, the material, and the polymer can be synthesized at room temperature using a sol-gel method as the silica precursor. Hydrolysis and condensation reaction of the silica precursor can be conducted in the presence of the polymer and the material. Additional details regarding methods of synthesis are provided in Example 2.

In an embodiment, the composite material can be disposed on a surface (e.g., in situ). The composite material can form a film (e.g., about 0.1 mm to 2 mm thick) that can act as a barrier to inhibit or substantially inhibit (e.g., about 70 to 99%, about 80 to 99%, or about 90 to 99%) the transmission of a disease such as HLB. In an embodiment, the film can be used to prevent or substantially prevent organisms from transmitting diseases such as ACPs from transmitting HLB.

EXAMPLES

Example 1

Citrus greening (also called Huanglongbing, HLB) [1, 2] and citrus canker [3, 4] are the two most devastating citrus diseases affecting the citrus industry worldwide. In Florida, the 9 billion dollar citrus industry is being negatively affected by HLB infection, which has spread throughout all of the commercial groves. The vector for HLB disease causing bacteria (*Candidatus Liberibacter asiaticus [*6-8]) transmission is a small, phloem-feeding insect (about one-eighth of an inch) known as Asian Citrus Psyllid (ACP, *Diaphorina citri*). ACPs are more commonly attracted to young trees than mature trees since younger trees produce multiple flushes throughout the year. Once a citrus tree is infected with HLB, it will eventually die. While citrus canker spreading can be minimized by aggressive copper (Cu) spraying [4] and windbreak programs [3, 5], there is currently no cure available for HLB infection [2].

Controlling ACPs with insecticides or altering ACP feeding behavior with repellants is a realistic approach to prevent HLB spreading [6]. The efficacy of several potent insecticides (such as imidacloprid, clothianidin, fenpropathrin, chlorpyrifos and thiamethoxam) has been evaluated over the past several years [7-9] in a number of field trials. Results from these studies suggested that these insecticides are effective in controlling ACP populations despite some variations observed due to application methods [7-9]. Currently, three soil applied insecticides, imidacloprid, thiamethoxam, and clothianidin are available for systemically controlling ACP infestation on young nonbearing trees. Unfortunately, for bearing trees, foliar application is the only permitted option which has limited success. Moreover, foliar application of insecticides may negatively impact natural ACP antagonists, such as ladybeetles and parasitic wasps.

The ability for ACPs to development resistance to insecticides due to repeated applications is a serious concern [8]. Efficacy of chemical and film based ACP repellants have been tested in the field [7, 9-11]. Sulfur volatiles [11] such as dimethyldisulfide (DMDS) and essential oils [12, 13] such as coriander, thyme, rose and lavender are some common chemical repellants which have shown moderate ACP repellant properties. However, due to the lack of suitable application methods, it is challenging to effectively implement these chemical repellants in commercial groves. Kaolin clay mineral (Aluminosilicate) particulates (a product from NovaSource, brand name "Surround® WP") have been used in field trials as a film-based ACP repellant [14]. Trial results have shown good efficacy of Kaolin clay material in altering ACP feeding behavior [10, 14]. On the other hand, poor rain-fastness of this clay material severely limits its practical application for use only during the dry season in Florida [14]. In addition, due to its natural white powdery appearance, Kaolin clay masks HLB symptoms on the leaf surface. There is a pressing need for a robust film-based barrier material capable of protecting citrus crops from ACP invasion.

In Example describes an environment-friendly non-phytotoxic organo-silica based composite film (OSCF) material as a potential ACP repellent. This film will serve as a barrier and therefore expected to disrupt the phloem feeding behavior of ACPs through its unique ("hard" and "sticky") mechanical properties.

Currently, there is no therapy available for citrus growers worldwide to mitigate HLB infection. For that reason, minimizing HLB disease spreading by preventing invasion of ACPs to HLB free groves is the most attractive solution. Embodiments of the present disclosure has the ability to strongly adhere to the plant surface, which should provide an efficient barrier ("hard" and "sticky") against ACPs, resulting in altered phloem feeding behavior.

Embodiments of the present disclosure include a combination of silica and PAM using plant nutrient based ionic cross-linker such as $Ca^{2+}$ and $Mg^{2+}$ ions. During the nucleation and growth processes of silica nanoparticle or silica nanogel SiNP or NG material (in situ), PAM polymer chains are chemically cross-linked at the molecular/nanoparticle level in the presence of a plant nutrient based ionic cross-linker. The resulting composite material is a composite (hybrid) of inorganic (silica sol-gel or colloidal silica particles and ionic cross-linker; referred to as "Hard") and organic (PAM; referred as "Sticky") material.

The material ingredients of embodiments of the present disclosure are EPA approved for agricultural applications.

Silica dust and silica gel were approved in 1960 for use in insecticides and acaricides[15], and also approved as inert ingredients for use in combination with other pesticides[16]. PAM is approved by the EPA as a flocculant for sewage and waste water treatment and also as a soil conditioner[17]. PAM forms complexes with Ca[18] and Mg[19] salts. The strong interaction of these ions with silica is well known (calcium silicate[20], and magnesium silicate[21], "Talc").

There is a clear advantage to preparing embodiments of the composite material via in situ synthesis as opposed to preparing a formula by mixing pre-synthesized SiNP or NG materials with PAM. In situ synthesis method is expected to increase molecular interactions between silica and PAM (intermolecular forces) resulting in enhanced entanglement of PAM polymer chains with SiNP or NG matrix. Ionic cross-linkers will further increase interactions of PAM polymer chains with the SiNP or NG matrix via covalent cross-linking.

Table 1 summarizes characteristics of the proposed OSCF material in comparison with Kaolin clay (such as Surround®) product) and chemical repellents such as sulfur based volatiles. Many sulfur based plant volatiles are known to cause phytotoxicity to plants[22].

PAM, SiNP and SiNG. Talc and PAM; all of which showed poor rainfastness by completely washing off from the leaf surfaces.

FIG. 1 illustrates digital photographs of some representative citrus leaf surfaces before and after rigorous spray washing with water (simulating over 6 inches of rainfall). Phytotoxicity studies were carried out using *Vinca* sp. (an ornamental plant, highly susceptible to phytotoxicity; purchased from Home Depot).

FIG. 2 shows digital images of *vinca* leaf surface showing no sign of phytotoxicity even after 72 hrs post treatment with SiNP-PAM and SiNG-PAM film materials.

Field Emission-Scanning Electron Microscopy (FE-SEM) technique was used to characterize SiNP-PAM and SiNG-PAM film materials deposited on citrus (Lime) leaf surface. For SEM sample preparation film material was spray-applied liberally to citrus leaf surface until excess liquid formula began to drip. Once the film was dried, applying over six inches rainfall was simulated in an attempt to wash off film from leaf surface. FE-SEM images of SiNG-PAM and SiNP-PAM are shown in FIG. 3A and FIG. 3C, respectively. The SiNG-PAM film shows moderately smooth surface topography whereas the SiNP-PAM film

TABLE 1

Example 1, Comparison of material characteristics of OSCF nanogel, OSCF nanoparticle, SiNP/NG-PAM, SiNP/NG, PAM, chemical volatiles (e.g. sulfur volatiles) and Kaolin-Clay (e.g. Surround®).

| | Proposed ACP repellents | | | | | | |
|---|---|---|---|---|---|---|---|
| Characteristics | Proposed OSCF nanogel material | Proposed OSCF nanoparticle material | SiNP/NG-PAM (control) | SiNP/NG (control) | PAM (control) | Kaolin-Clay (control) | Chemical volatiles |
| Rainfastness | High | Moderate-high | Moderate | Moderate | Low | Very low | N/A |
| Phytotoxicity | None | None | None | None | None | None | Moderate-High |
| Transparency | High | Moderate (SiNP size dependent) | Moderate (SiNP)-high (SiNG) | Moderate (SiNP)-high (SiNG) | High | Non-transparent | N/A |
| Colloidal stability | High | Moderate to high | Moderate | Moderate | Highly water soluble | Low | N/A |
| Chemical stability | Moderate-high | Moderate-high | High | High | Low | High | Moderate |
| Film thickness manipulability | High | High | Moderate | Moderate | Moderate | Moderate | N/A |
| Film porosity manipulability | High | High | Moderate | Moderate | Moderate | Low | N/A |
| Film hardness manipulability | Moderate | Moderate-High | Moderate-high | Moderate-high | Low | None (natural material) | N/A |

Experimental Approach
Preliminary Results

The OSCF-nanogel film material was synthesized in situ by acid-catalyzed hydrolysis of TEOS in water, whereas the OSCF-nanoparticle film material was synthesized in situ by base-catalyzed hydrolysis of TEOS in a water-ethanol mixed-solvent system in the presence of calcium ion cross-linker. SiNG-PAM and SiNP-PAM film materials were similarly synthesized in absence of ionic cross-linker. Rainfastness studies were conducted on Lime citrus variety using several film materials including two OSCF materials: SiNG-PAM, SiNP-PAM, PAM, SiNG, SiNP and Talc. The two OSCF materials with calcium ion cross-linking showed outstanding rainfastness as compared to SiNG-PAM, SiNP-shows somewhat rough surface topography. Rough surface topography of SiNP-PAM film arises due to the presence of SiNP clusters which are embedded within the PAM matrix. SiNG-PAM and SiNP-PAM films were characterized by Atomic Force Microscopy (AFM). FIG. 3B and FIG. 3D shows AFM images of SiNG-PAM and SiNP-PAM films, respectively on mica surface. AFM surface topography was similar to what was seen in FE-SEM for both film materials.

To understand the interaction of PAM with SiNP/NG materials at the molecular level, UV-Vis, $^1$H NMR and FT-IR spectroscopy techniques were used. PAM characteristic absorption peak at 337 nm appeared in both OSCF nanogel and OSCF nanoparticle samples. It was interesting to see that OSCF nanoparticle and PAM absorption spectra were similar whereas the OSCF nanogel spectrum shifted towards the silica nanogel spectrum. Note that silica to PAM weight ratio in both OSCF samples was kept identical. This suggests that SiNG-PAM strongly interacted at the molecular level during the nucleation and growth of SiNG material. In OSCF nanoparticle material SiNPs form clusters and remain embedded in the PAM matrix.

Therefore, UV-Vis spectra of OSCF nanoparticle and PAM were similar. SiNPs aggregate in water and contribute to light scattering. As a result, SiNP colloidal suspension is opaque in comparison to SiNG which is completely transparent. Zeta potential is a measurement of surface charge. Zeta potential values of OSCF nanogel and OSCF nanoparticles were measured to be +0.9 mV and −43.0 mV, respectively. Zeta potential values clearly suggest that OSCF film apparently possesses no surface charge, suggesting that silica silanol (Si—OH) groups are not dissociated in presence of PAM and therefore engaged in strong hydrogen bonding with PAM. High negative zeta potential value of OSCF nanoparticle is indicative of weak interaction between SiNP and PAM, resulting in SiNP segregation. An interesting observation was made with OSCF nanogel material producing a pungent odor. OSCF nanoparticle, SiNG-PAM, SiNP-PAM, PAM, calcium chloride (ionic cross-linker), SiNG, SiNP and TEOS (silica precursor) did not have any strong odor. This indicates that OSCF-nanogel is a new material with distinct chemical characteristics. It also explains why OSCF nanogel material is "sticky" and exhibits superior rainfastness.

Fourier Transform Infra-red (FT-IR) spectra of SiNG-PAM and PAM were similar. A characteristic FT-IR peak of PAM at 2935 $cm^{-1}$ [23] (C—H stretch) was present in both SiNG-PAM and SiNP-PAM. Similarly, a characteristic silica Si—O peak at 1040 $cm^{-1}$ [23] was present in SiNG, SiNG-PAM and SiNP-PAM. Interestingly, a strong FT-IR peak that appeared at 1098 $cm^{-1}$ (characteristic to Si—O stretching [24, 25]) was observed in SiNP-PAM but not in SiNG-PAM. This suggests that silica chemical signature is somewhat compromised in SiNG-PAM material. Transmittance ratio of C=O stretching (1649 $cm^{-1}$) to N—H bending (1603 $cm^{-1}$) was estimated to be 1.04 (PAM), 1.06 (SiNG-PAM) and 1.12 (SiNP-PAM). This further indicates that silica chemical characteristics is somewhat compromised in SiNG-PAM material although weight ratio of PAM to silica remained identical. The PAM polymer is composed of repeating acrylamide units.

$H^1$ NMR spectrum of acrylamide shows peaks at 1.5 ppm and 2.2 ppm corresponding to the methyl and $CH_2$ groups. The AB pattern of the chiral proton is represented at 2.6 ppm, 2.8 ppm, and 3.1 ppm because of the changing proximity of the chiral proton to adjacent functional groups in the polymer. While the $^1H$ NMR spectroscopy of SiNG-PAM contains the same proton peaks as acrylamide, the $^1H$ NMR spectroscopy of SiNP-PAM only shows proton peaks that correspond to the methyl and $CH_2$ groups. Regardless, the data shows that both SiNG-PAM and SiNP-PAM contain PAM. FT-IR, $H^1$ NMR and UV-Vis results support unique molecular interaction between SiNG and PAM.

Synthesize OSCF Material

Synthesis protocols originally developed for making copper (Cu) loaded SiNP/NG materials [26, 27] (using previous CRDF support; project numbers 186, 328 and 554) will be adapted with further modification. Briefly, the OSCF material will be synthesized at room temperature using a sol-gel method using tetraethylorthosilicate (TEOS, a silane reagent) as the silica precursor. Hydrolysis and condensation reaction of the silica precursor will be initiated using a catalyst (a mineral acid or base) in the presence of PAM and a plant-nutrient based bivalent ionic cross-linker (gelator) such as calcium ($Ca^{2+}$) or magnesium ($Mg^{2+}$) ions. PAM forms complexes with Ca[18] and Mg[19] salts. Therefore, a ternary system of SiNP/NG-ionic crosslinker-PAM is a new material. These ionic cross-linkers will bridge between the Si—OH group of silica and the amide group of PAM, thus facilitating binding of PAM to SiNP/NG. Film porosity and hardness will be manipulated by controlling the weight ratio of SiNP/NG to PAM to ionic cross-linker. In this study PAM of molecular weight ~10 kD will be used to facilitate intermolecular interactions with silica matrix. A series of OSCF materials will be synthesized by varying the ratio of TEOS to PAM (wt/wt %). The effect of pH on the colloidal stability (gelation property) of the OSCF aqueous suspension in the range between 4 and 9 will be assessed by monitoring changes in viscosity. Optimization of OSCF formulations will be geared towards exhibiting strong rainfastness (retention properties) and minimal (or no) phytotoxic properties at different spray concentrations. We will also prepare appropriate controls as discussed in the preliminary results section. We will also prepare OSCF materials by mixing pre-prepared silica gel (or silica nanoparticles) with ionic cross-linker and PAM (at the same wt/wt % ratio of TEOS to PAM) for efficacy comparison purposes. Kaolin (clay-based; aluminosilicate mineral) will be used as the standard (control).

Example 2

Synthesis of Organo Silica Composition Formulations (OSCF)

Magnesium chloride hexahydrate ($MgCl_2.6H_2O$) (CAS#7791-18-6) (Fisher Scientific)

Calcium Chloride dihydrate ($CaCl_2.2H_2O$) (CAS#10035-04-8) (Fisher Scientific)

Zinc Oxide 800 (ZnO) (CAS #1314-13-2) (Zinc Oxide, LLC)

Copper Hydroxide (65% Metallic Cu)

Ethanol (ETOH) (95%) (190 Proof)—Ethyl Alcohol (CAS#64-17-5) (Decon Laboratories Inc)

Hydrochloric Acid (conc HCL)—(CAS#7647-01-0) (Fisher Scientific)

Sodium Hydroxide (1M & 4M NaOH) (CAS#1310-73-2) (Fisher Scientific)

Tetraethylorthosilicate (TEOS) (CAS#78-10-4) (Gelest Inc)

Polyvinylpyrrolidone (PVP) 40% wt (CAS#9003-39-8) (Acros Organics)

Polyacrylamide (PAM) 50% wt (CAS #9003-05-8) (CarboMer Inc)

Kaolin Clay (CAS #1332-58-7)

Sodium Silicate 37% wt (CAS #6834-92-0) (Fisher Scientific)

Deionized $H_2O$— Barnstead Nanopure Diamond

OS-SG 1

0.136 g of $Cu(OH)_2$ (65% Metallic Cu) was added to 0.5 mL of EtOH along with 24 mL of deionized $H_2O$. This mixture was set to stir while slowly adding 0.27 mL of 1% HCL. An additional 0.212 mL of TEOS was added dropwise and left to stir for 16-24 hrs. PAM (50% wt) was then measured out and 5 mL was added to the stirring mixture and left for 16-24 hrs. Total Volume=~30 mL pH=~2

OS-SG 2

0.5 mL of EtOH along with 25 mL of deionized $H_2O$. This mixture was set to stir while slowly adding 0.27 mL of 1%

HCL. An additional 0.212 mL of TEOS was added dropwise and left to stir for 16-24 hrs. PAM (50% wt) was then measured out and 5 mL was added to the stirring mixture and left for 16-24 hrs. Total Volume=~30 mL pH=~4

OS-SG 3

1.08 g of $CaCl_2.2H_2O$ (27.3% Metallic Ca) was added to 81.34 mL of deionized $H_2O$. This mixture was set to stir while slowly adding 0.9 mL of 1% HCL. An additional 0.707 mL of TEOS was added dropwise and left to stir for 16-24 hrs. PAM (50%) was then measured out and 16.67 mL was added to the stirring mixture and left for 16-24 hrs. pH was raised to ~8 with 2 mL of 1 M NaOH. Total Volume=~100 mL

OS-SG 4

2.45 g of $MgCl_2.6H_2O$ (11.9% Metallic Ca) was added to 80.16 mL of deionized $H_2O$. This mixture was set to stir while slowly adding 0.9 mL of 1% HCL. An additional 0.707 mL of TEOS was added dropwise and left to stir for 16-24 hrs. PAM (50% wt) was then measured out and 16.67 mL was added to the stirring mixture and left for 16-24 hrs. pH was raised to ~8 with 3 mL of 1 M NaOH. Total Volume=~100 mL

OS-SG 5

10 mL of EtOH along with 40 mL of deionized $H_2O$. This mixture was set to stir while slowly adding 2.0 mL of conc. HCL. An additional 4.5 mL of TEOS was added dropwise and left to stir for 2 hrs. PAM (50% wt) was then measured out and 25 mL was added to the stirring mixture and left for 16-24 hrs. pH was raised to ~8 with 5 mL of 4 M NaOH Total Volume=~85 mL

OS-SG 6

10 mL of EtOH along with 40 mL of deionized $H_2O$. This mixture was set to stir while slowly adding 2.0 mL of conc. HCL. An additional 4.5 mL of TEOS was added dropwise and left to stir for 2 hrs. PVP (40% wt) was then measured out and 25 mL was added to the stirring mixture and left for 16-24 hrs. pH was raised to ~8 with 6 mL of 4 M NaOH Total Volume=~86 mL

OS-SG 7

13.3 g of $CaCl_2.2H_2O$ (27.3% Metallic Ca) was added to 10 mL of EtOH along with 30 mL of deionized $H_2O$. This mixture was set to stir while slowly adding 2.0 mL of conc. HCL. An additional 4.5 mL of TEOS was added dropwise and left to stir for 2 hrs. PAM (50% wt) was then measured out and 25 mL was added to the stirring mixture and left for 16-24 hrs. pH was raised to ~8 with 5 mL of 4 M NaOH Total Volume=~84 mL

OS-SG 8

13.3 g of $CaCl_2.2H_2O$ (27.3% Metallic Ca) was added to 10 mL of EtOH along with 30 mL of deionized $H_2O$. This mixture was set to stir while slowly adding 2.0 mL of conc. HCL. An additional 4.5 mL of TEOS was added dropwise and left to stir for 2 hrs. PVP (40% wt) was then measured out and 25 mL was added to the stirring mixture and left for 16-24 hrs. pH was raised to ~8 with 6 mL of 4 M NaOH Total Volume=~84 mL

OS-SG 9

30 g of $MgCl_2.6H_2O$ (11.9% Metallic Mg) was added to 10 mL of EtOH along with 20 mL of deionized $H_2O$. This mixture was set to stir while slowly adding 2.0 mL of conc. HCL. An additional 4.5 mL of TEOS was added dropwise and left to stir for 2 hrs. PAM (50% wt) was then measured out and 25 mL was added to the stirring mixture and left for 16-24 hrs. pH was raised to ~8 with 7 mL of 4 M NaOH Total Volume=~88 mL

OS-SG 10

30 g of $MgCl_2.6H_2O$ (11.9% Metallic Mg) was added to 10 mL of EtOH along with 20 mL of deionized $H_2O$. This mixture was set to stir while slowly adding 2.0 mL of conc. HCL. An additional 4.5 mL of TEOS was added dropwise and left to stir for 2 hrs. PVP (40% wt) was then measured out and 25 mL was added to the stirring mixture and left for 16-24 hrs. pH was raised to ~8 with 8 mL of 4 M NaOH Total Volume=~89 mL

OS-SG 11

2 g of ZnO (80% Metallic Zn) was added to 2 mL of PAM (50% wt). The volume of this mixture was then increased to 20 mL with deionized $H_2O$. This mixture was set to stir for 10 minutes. An additional 2.0 mL of sodium silicate was added dropwise and left to stir for 2 hrs Total Volume=~26 mL

OS-SG 12

2 g of kaolin clay was added to 2 mL of PAM (50% wt). The volume of this mixture was then increased to 20 mL with deionized $H_2O$. This mixture was set to stir for 10 minutes. An additional 2.0 mL of sodium silicate was added dropwise and left to stir for 2 hrs Total Volume=~26 mL

TABLE 1

Example 2: Summary of the composition of OSCF materials.

| | Silica Reagent | Polymer (mL) | Metal/ Crosslinker (g) | EtOH (mL) | $H_2O$ (mL) | HCl (mL) (conc or 1%) | NaOH (mL) (1 or 4M) | Avg. Total Volume (mL) |
|---|---|---|---|---|---|---|---|---|
| OS-SG 1 | 0.212 TEOS | 5 PAM | 0.136 $Cu(OH)_2$ | 0.5 | 24 | 0.27 | — | 30 |
| OS-SG 2 | 0.212 TEOS | 5 PAM | — | 0.5 | 25 | 0.27 | — | 30 |
| OS-SG 3 | 0.707 TEOS | 16.67 PAM | 1.08 $CaCl_2$ | — | 81.34 | 0.9 | 2 | 100 |
| OS-SG 4 | 0.707 TEOS | 16.67 PAM | 2.45 $MgCl_2$ | — | 80.16 | 0.9 | 3 | 100 |
| OS-SG 5 | 4.5 TEOS | 25 PAM | — | 10.0 | 40 | 2.0 | 5 | 85 |
| OS-SG 6 | 4.5 TEOS | 25 PVP | — | 10.0 | 40 | 2.6 | 6 | 86 |
| OS-SG 7 | 4.5 TEOS | 25 PAM | 13.3 $CaCl_2$ | 10.0 | 30 | 2.0 | 5 | 84 |
| OS-SG 8 | 4.5 TEOS | 25 PVP | 13.3 $CaCl_2$ | 10.0 | 30 | 2.0 | 6 | 84 |
| OS-SG 9 | 4.5 TEOS | 25 PAM | 30.0 $MgCl_2$ | 10.0 | 20 | 2.0 | 7 | 88 |
| OS-SG 10 | 4.5 TEOS | 25 PVP | 30.0 $MgCl_2$ | 10.0 | 20 | 2.0 | 8 | 89 |
| OS-SG 11 | 2.0 $Na_2SiO_3$ | 2.0 PAM | 2.0 ZnO | — | 20 | — | — | 26 |
| OS-SG 12 | 2.0 $Na_2SiO_3$ | 2.0 PAM | 2.0 kaolin clay | — | 20 | — | — | 26 |

Tables 2 and 3, Example 2, illustrate phytotoxicity testing of embodiments of the present disclosure.

TABLE 2

Example 2

| | Vinca sp Time (hr) | | | Citrus (Persian Lime) Time (hr) | | |
|---|---|---|---|---|---|---|
| | 24 | 48 | 72 | 24 | 48 | 72 |
| OS-SG 5 | − | − | − | − | − | − |
| OS-SG 6 | − | − | − | − | − | − |
| OS-SG 7 | − | − | − | − | − | − |
| OS-SG 8 | − | − | − | − | − | − |
| OS-SG 9 | − | − | − | − | − | − |
| OS-SG 10 | − | − | − | − | − | − |
| CuSO$_4$ | + | ++ | +++ | + | ++ | +++ |
| Kaolin Clay | − | − | − | − | − | − |

− No plant tissue damage, +, ++ and +++ Minimal, moderate and severe plant tissue damage.

TABLE 3

Example 2

| | Vinca sp Time (hr) | | | Tomato sp Time (hr) | | |
|---|---|---|---|---|---|---|
| | 24 | 48 | 72 | 24 | 48 | 72 |
| OS-SG 11 | − | − | − | − | − | − |
| OS-SG 12 | − | − | − | − | − | − |
| CuSO$_4$ | + | ++ | +++ | + | ++ | +++ |
| (Kaolin Clay) | − | − | − | − | − | − |

− No plant tissue damage, +, ++ and +++ Minimal, moderate and severe plant tissue damage.

FIG. 4 is a graph illustrating the temperature safety testing for OSCF materials. All OSCF tested except OS-SG 8 and 9 do not exhibit significant temperature variance in comparison to kaolin clay control.

Figure 5:
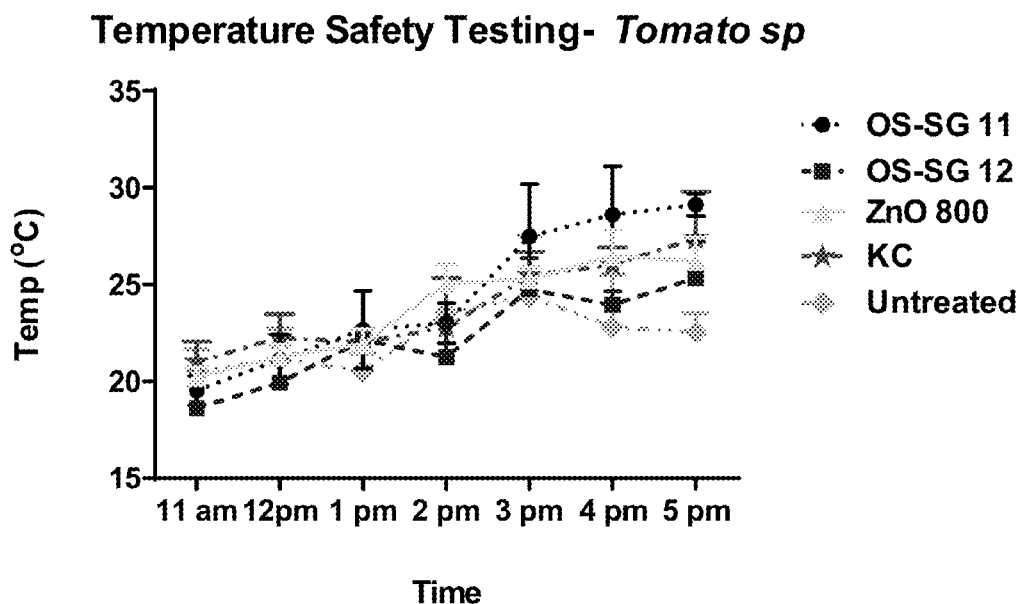
FIG. 5 is a graph illustrating the temperature safety testing for OSCF materials. All OSCF tested do not exhibit significant temperature variance in comparison to kaolin clay control.

FIG. 5 is a graph illustrating the temperature safety testing for OSCF materials. All OSCF tested do not exhibit significant temperature variance in comparison to kaolin clay control.

Figure 6:
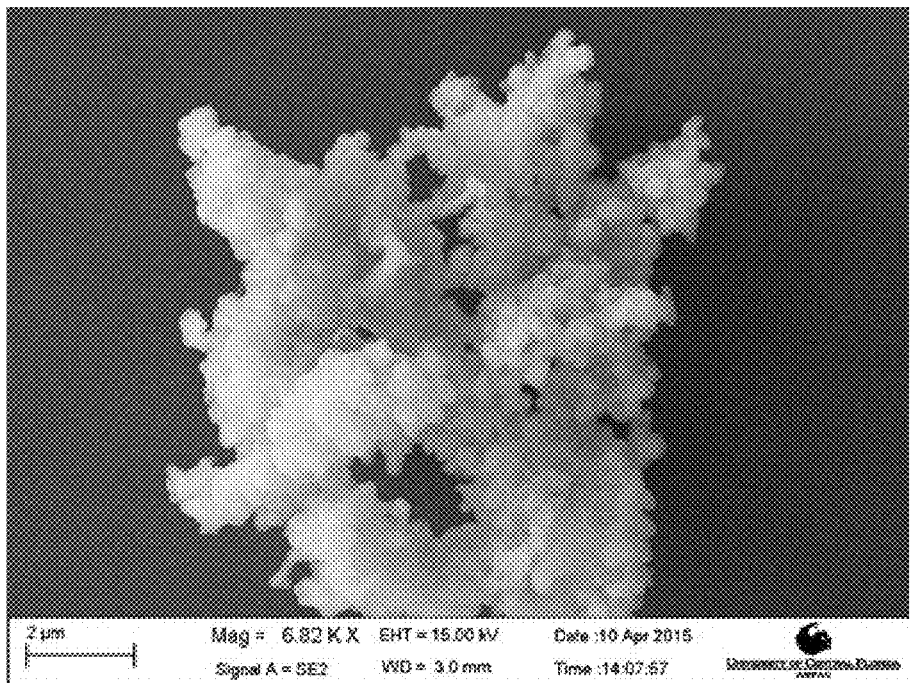
FIG. 6 illustrates a SEM image of OS-SG 11 revealed irregular shaped particulate clusters with sizes >1 micron.

FIG. 6 illustrates a SEM image of OS-SG 11 revealed irregular shaped particulate clusters with sizes >1 micron.

Figure 7:
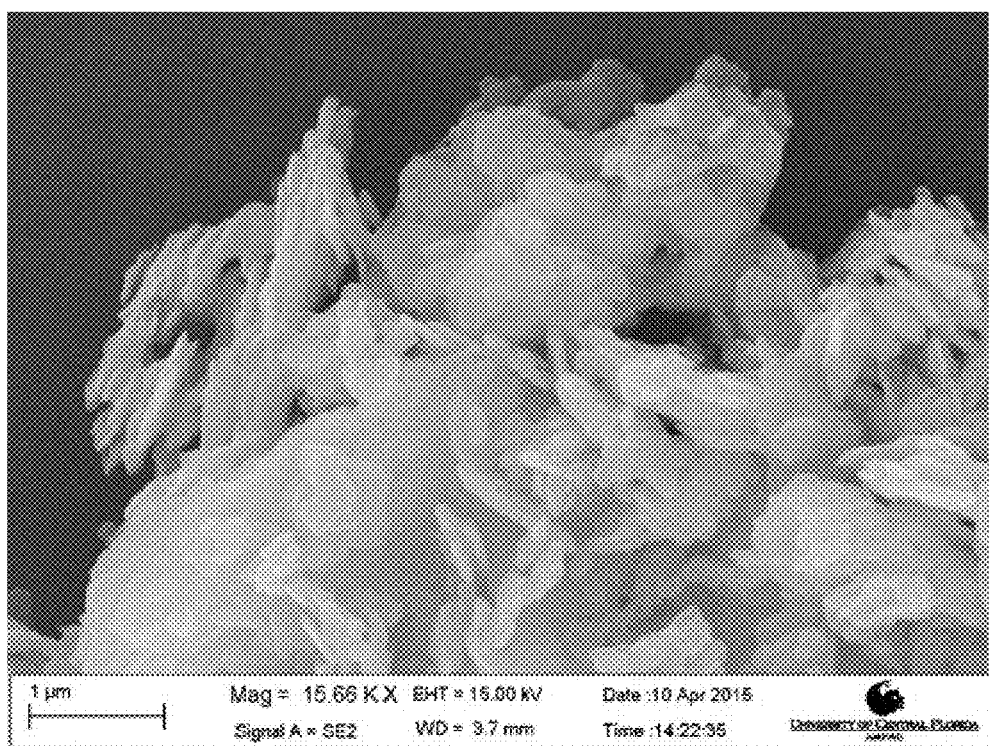
FIG. 7 illustrates a SEM image of OS-SG 12 revealed irregular shaped layered sheets clusters with sizes >1 micron.

FIG. 7 illustrates a SEM image of OS-SG 12 revealed irregular shaped layered sheets clusters with sizes >1 micron.

Figure 8:
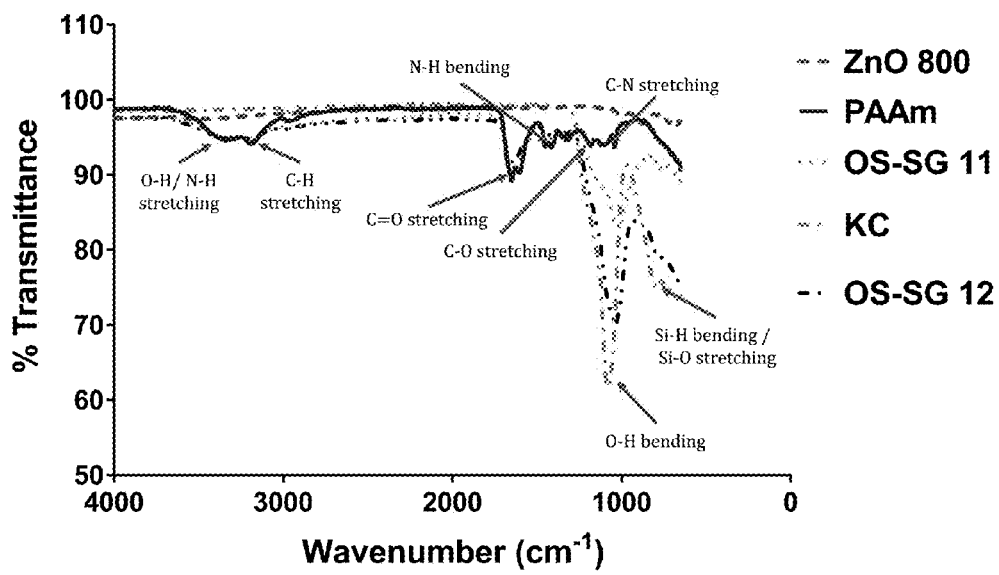
FIG. 8 illustrates FTIR spectra that confirm the presence of polymer (PAM) within OS-SG 11 and 12.

FIG. 8 illustrates FTIR spectra that confirm the presence of polymer (PAM) within OS-SG 11 and 12.

Figure 9:
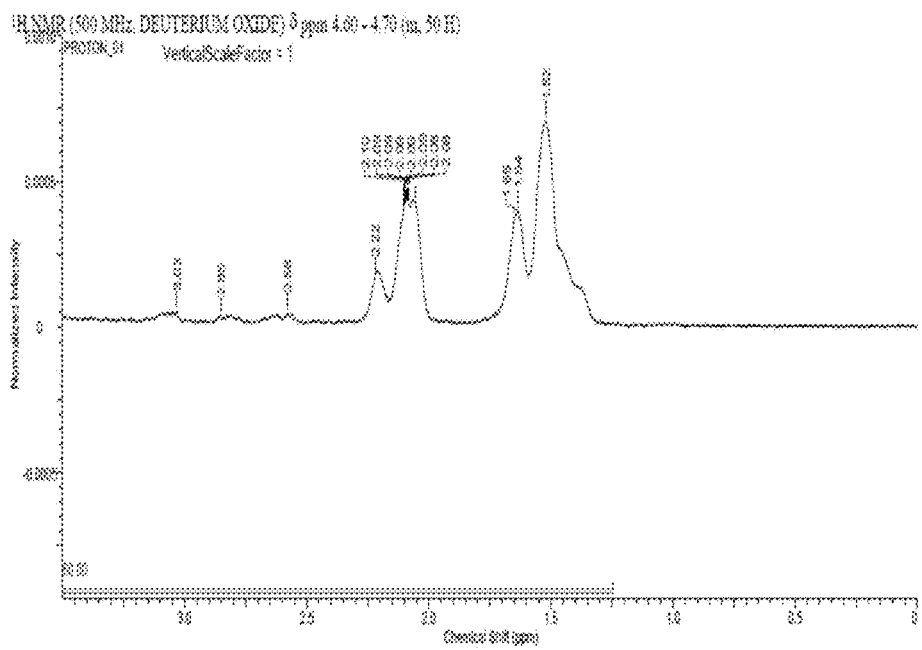
FIG. 9 illustrates distinct peaks for PAM detected in $H^1$ NMR.

FIG. 9 illustrates distinct peaks for PAM detected in H$^1$ NMR.

Figure 10:
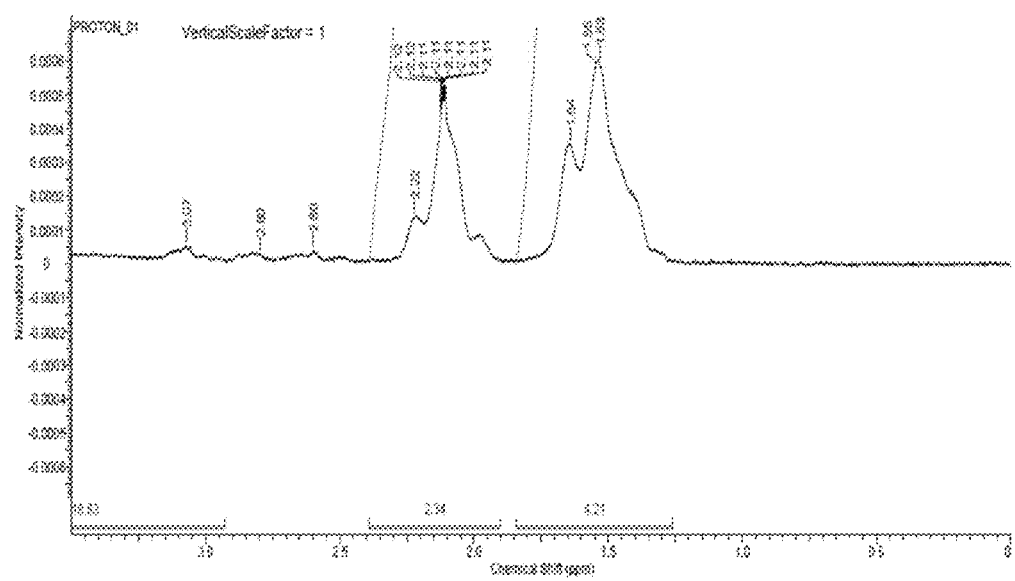
FIG. 10 illustrates distinct peaks for PAM detected in $H^1$ NMR, which confirms presence of PAM in OS-SG 11 material.

FIG. 10 illustrates distinct peaks for PAM detected in H$^1$ NMR, which confirms presence of PAM in OS-SG 11 material.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to measurement techniques and the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

Therefore, at least the following is claimed:

1. A formulation comprising:
    a silicon-based material that is crosslinked to a polymer to form an organo-silica-based composite material, wherein the polymer is selected from the group consisting of: polyvinylpyrrolidone, polyacrylamide, polylactic acid, polyglycolic acid, chitosan, dextran, polyethyleneglycol, polyvinylalcohol, and a combination thereof; and
    a material that is crosslinked to the silicon-based material and the polymer via intermolecular forces, the material being selected from the group consisting of a kaolin and a zinc oxide (ZnO) material, wherein the formulation upon being coated on a surface of a structure forms an organo-silica-based composite film that has an enhanced rainfastness relative to that of either the silicon-based material or the polymer.

2. The formulation of claim 1, wherein the silicon-based material is selected from the group consisting of: silica nanogel, silica nanoparticles, and a combination thereof.

3. The formulation of claim 1, further comprising a crosslinker, wherein the crosslinker enhances crosslinking between the polymer and the silicon-based material.

4. The formulation of claim 1, wherein the polymer is about 40 to about 60 weight % of the dry composite and the silicon-based material is about 40 to about 60 weight % of the dry composite.

5. The formulation of claim 3, wherein the crosslinker is a metal ion, wherein the metal ion is selected from the group consisting of: $Ca^{2+}$, $Mg^{2+}$, $Zn^{2+}$, $Al^{3+}$, $Cu^{2+}$, and a combination thereof.

6. The formulation of claim 5, wherein the crosslinker is about 10 to about 20 weight % of the dry composite, the polymer is about 30 to about 40 weight % of the dry composite, and the silicon-based material is about 30 to about 40 weight % of the dry composite.

7. The formulation of claim 6, wherein the polymer is polyacrylamide.

8. The formulation of claim 2, wherein the silicon-based material is a silica nanogel.

9. The formulation of claim 8, wherein the polymer is polyacrylamide.

10. The formulation of claim 8, wherein the material is about 10 to about 40 weight % of the dry composite, the polymer is about 20 to about 50 weight % of the dry composite, and the silicon-based material is about 20 to about 40 weight % of the dry composite.

11. A method for inhibiting the transmission of an insect-transmitted plant disease, comprising:
    disposing a formulation over or onto a surface of a structure to provide an organo-silica-based composite film on the surface thereof, wherein the organo-silica-based composite film includes a silicon-based material that is crosslinked to a polymer to form an organo-silica-based composite material, the polymer being selected from the group consisting of: polyvinylpyrrolidone, polyacrylamide, polylactic acid, polyglycolic acid, chitosan, dextran, polyethyleneglycol, polyvinylalcohol, and a combination thereof; and a material that is crosslinked to the silicon-based material and the polymer via intermolecular forces, the material being selected from the group consisting of a kaolin and a zinc oxide (ZnO) material; and wherein the organo-silica-based composite film has an enhanced rainfastness relative to that of either the silicon-based material or the polymer.

12. The method of claim 11, wherein the insect-transmitted plant disease is selected from at least one of a Huanglongbing (HLB) disease and a Pierce's disease.

13. The method of claim 11, wherein disposing includes disposing the formulation on the surface of the structure in situ.

14. The method of claim 11, further comprising forming a barrier on the surface of the structure.

15. A method for preventing an insect from transmitting an insect-borne plant disease, comprising:
disposing a formulation over a surface of a structure to form an organo-silica-based composite film on the surface in situ, wherein the organo-silica-based composite film includes a silicon-based material, that is crosslinked to a polymer, the polymer being selected from the group consisting of: polyvinylpyrrolidone, polyacrylamide, polylactic acid, polyglycolic acid, chitosan, dextran, polyethyleneglycol, polyvinylalcohol, and a combination thereof, and a material that is crosslinked to the silicon-based material and the polymer via intermolecular forces, the material being selected from the group consisting of a kaolin and a zinc oxide (ZnO) material, and wherein the organo-silica-based composite film has an enhanced rainfastness relative to that of either the silicon-based material and the polymer.

16. The formulation of claim 3, wherein the crosslinker is bound to the silicon-based material and the polymer via a metal-ligand complex.

17. The formulation of claim 3, wherein the crosslinker is an ionic crosslinker that binds the silicon-based material and the polymer via covalent cross-linking.

18. The formulation of claim 1, wherein the organo-silica-based composite film provides a barrier that prevents an insect from transmitting an insect-borne plant disease, the insect being at least one of an Asian Citrus Psyllid (ACP) and a Sharpshooter.

19. The formulation of claim 1, wherein the organo-silica-based composite film inhibits transmission of an insect-infested plant disease, the insect-infested plant disease being at least one of a Huanglongbing (HLB) disease and a Pierce's disease.

20. The method of claim 11, wherein the organo-silica-based composite film further comprises a crosslinker that enhances the crosslinking between the silicon-based material and the polymer, the crosslinker comprising a metal ion.

21. The method of claim 20, wherein the crosslinker is bound to the silicon-based material and the polymer via a metal-ligand complex.

22. The method of claim 20, wherein the crosslinker is an ionic crosslinker that binds the silicon-based material and the polymer via covalent cross-linking.

23. The method of claim 15, wherein the insect is at least one of an Asian Citrus Psyllid (ACP) that transmits Huanglongbing (HLB) disease and a Sharpshooter that transmits Pierce's disease.

24. The method of claim 15, wherein the organo-silica-based composite film further comprises a crosslinker that enhances the crosslinking between the silicon-based material and the polymer, the crosslinker comprising a metal ion.

25. The method of claim 24, wherein the crosslinker is bound to the silicon-based material and the polymer via a metal-ligand complex.

26. The method of claim 24, wherein the crosslinker is an ionic crosslinker that binds the silicon-based material and the polymer via covalent cross-linking.

27. A composite film comprising:
an organo-silica-based formulation in a solvent, the organo-silica-based formulation comprising a silicon-based material, that is crosslinked to a polymer selected from the group consisting of: polyvinylpyrrolidone, polyacrylamide, polylactic acid, polyglycolic acid, chitosan, dextran, polyethyleneglycol, polyvinylalcohol, and a combination thereof, and a material that is crosslinked to the silicon-based material and the polymer via intermolecular forces, the material being selected from the group consisting of a kaolin and a zinc oxide (ZnO) material.

28. The composite film of claim 27, further comprising a crosslinker, wherein the crosslinker enhances the crosslinking between the silicon-based material and the polymer.

29. The composite film of claim 28, wherein the crosslinker is bound to the silicon-based material and the polymer via a metal-ligand complex.

30. The composite film of claim 28, wherein the crosslinker is an ionic crosslinker, wherein the ionic crosslinker binds the silicon-based material and the polymer via covalent cross-linking.

31. The formulation of claim 1, further comprising a solvent, the solvent being at least one of an organic solvent and an aqueous solvent.

32. The formulation of claim 1, wherein the organo-silica-based composite film has a first mechanical property, and a second, different mechanical property.

33. The composite film of claim 27, wherein the solvent comprises at least one of an organic solvent and an aqueous solvent.

34. The composite film of claim 27, wherein the organo-silica-based composite film has an enhanced rainfastness relative to that of either the silicon-based material or the polymer.

35. The method of claim 11, wherein the solvent comprises at least one of an organic solvent and an aqueous solvent.

36. The method of claim 11, wherein the organo-silica-based composite film has a first mechanical property, and a second, different mechanical property.

37. The method of claim 15, wherein the solvent comprises at least one of an organic solvent and an aqueous solvent.

38. The method of claim 15, wherein the organo-silica-based composite film has a first mechanical property, and a second, different mechanical property.

* * * * *